United States Patent
Ota

(10) Patent No.: US 12,064,322 B2
(45) Date of Patent: Aug. 20, 2024

(54) MOISTURE RETAINING BODY

(71) Applicant: PRIMULA MODESTA CO., LTD., Kitakyushu (JP)

(72) Inventor: Yumiko Ota, Kitakyushu (JP)

(73) Assignee: PRIMULA MODESTA CO., LTD., Kitakyushu (JP)

( * ) Notice: Subject to any disclaimer, the term of this patent is extended or adjusted under 35 U.S.C. 154(b) by 0 days.

(21) Appl. No.: 18/288,702

(22) PCT Filed: Apr. 17, 2022

(86) PCT No.: PCT/JP2022/017974
§ 371 (c)(1),
(2) Date: Oct. 27, 2023

(87) PCT Pub. No.: WO2022/230695
PCT Pub. Date: Nov. 3, 2022

(65) Prior Publication Data
US 2024/0207103 A1    Jun. 27, 2024

(30) Foreign Application Priority Data
Apr. 30, 2021  (JP) ................... 2021-076963

(51) Int. Cl.
*A61F 13/15* (2006.01)
*A61F 13/53* (2006.01)
*A61F 13/534* (2006.01)

(52) U.S. Cl.
CPC .......... *A61F 13/15252* (2013.01); *A61F 2013/15235* (2013.01); *A61F 2013/530007* (2013.01); *A61F 2013/530795* (2013.01); *A61F 2013/53445* (2013.01)

(58) Field of Classification Search
CPC ...... A61F 13/15252; A61F 2013/15235; A61F 2013/1526; A61F 2013/51433;
(Continued)

(56) References Cited

U.S. PATENT DOCUMENTS

| | | | | |
|---|---|---|---|---|
| 4,944,734 A * | 7/1990 | Wallach | ............... | A61F 13/512 604/364 |
| 6,747,186 B2 * | 6/2004 | Shimizu | ............ | A61F 13/51401 604/385.03 |
| 7,514,591 B2 * | 4/2009 | Przepasniak | ...... | A61F 13/15211 604/385.01 |

(Continued)

FOREIGN PATENT DOCUMENTS

| | | |
|---|---|---|
| JP | 04-114316 U1 | 10/1992 |
| JP | 06-101154 A | 4/1994 |

(Continued)

OTHER PUBLICATIONS

International Search Report and Written Opinion issued in International Application No. PCT/JP2022/017974, mailed Jun. 14, 2022, 10 pages.

*Primary Examiner* — Catharine L Anderson
(74) *Attorney, Agent, or Firm* — Talem IP Law, LLP

(57) ABSTRACT

Disclosed is a moisture-retaining body having a water-absorbing surface, having a structure in which, from a water-absorbing surface side, a water-permeable layer having water disintegrability and water permeability, a moisture-retaining layer having water disintegrability, water absorbability, and water retainability, a water-repellent layer including a water-soluble film and dots of a dot-like water-repellent resin with a diameter of 5 μm to 150 μm dispersed on a surface side of the water-soluble film facing the moisture-retaining layer, and a support layer having water disintegrability are sequentially laminated, as a moisture-retaining body which is quickly dissolved or decomposed by coming into contact with a large amount of water when (Continued)

dumped in a flush toilet or the like while being prevented from being dissolved or decomposed by retained moisture.

8 Claims, 1 Drawing Sheet

(58) Field of Classification Search
CPC ........ A61F 2013/530007; A61F 2013/530795; A61F 2013/53445; A61L 15/62
See application file for complete search history.

(56) References Cited

U.S. PATENT DOCUMENTS

| | | | | |
|---|---|---|---|---|
| 8,907,155 | B2* | 12/2014 | Wang | A61F 13/51478 604/364 |
| 2022/0062065 | A1* | 3/2022 | Koshy | A61F 13/15211 |

FOREIGN PATENT DOCUMENTS

| | | |
|---|---|---|
| JP | 07-324297 A | 12/1995 |
| JP | 10-005273 A | 1/1998 |
| JP | 3051660 U | 6/1998 |
| JP | 2000-34001 A | 2/2000 |
| JP | 2001-178776 A | 7/2001 |
| JP | 2002-306522 A | 10/2002 |
| JP | 3142751 U | 6/2008 |
| JP | 5841209 B2 | 1/2016 |

* cited by examiner

MOISTURE RETAINING BODY

CROSS-REFERENCE TO RELATED APPLICATIONS

This application is the U.S. National Stage Application of International Application No. PCT/JP2022/017974, filed Apr. 17, 2022, which claims priority to Japanese Patent Application Serial No. 2021-076963, filed Apr. 30, 2021, which are hereby incorporated by reference in their entirety.

TECHNICAL FIELD

The present invention relates to a moisture-retaining body that can be used in the fields of care, nursing, childcare, pet supplies, and the like.

BACKGROUND ART

Conventionally, paper diapers containing a high-molecular polymer intended for incineration as a main raw material have been generally used for treatment of wastes generated at sites of care, nursing, childcare, and the like. However, acceleration of global warming due to the generation of carbon dioxide accompanying incineration has become a social problem. In addition, it has not been possible to solve spread of pathogens and offensive odors contained in wastes into the surrounding atmosphere and unsanitary environment in which caregivers and the like are in danger of touching wastes, after use.

In view of such problems, the following inventions are known as inventions aimed at hygienic treatment of wastes.

For example, JP 2000-34001 A discloses, as a waste treatment bag capable of accommodating and holding such waste without a problem for a relatively long time even when the collected waste contains a relatively large amount of moisture, and further capable of being subjected to flush wastewater treatment, a waste treatment bag in which a water-dispersible paper is arranged on the outer side and a water-soluble film is arranged on the inner side to form a bag shape, in which both the water-dispersible paper and the water-soluble film are continuous in a folded shape at the bottom of the bag, and are substantially separated at the bottom of the bag, and are integrated at a site other than the bottom of the bag.

JP 3051660 U discloses a disposable waste treatment article dedicated to pet dogs and the like that can collect waste without staining hands and can utilize the characteristics of a water-soluble material to perform sewage treatment by using an antibacterial sheet paper having a water-soluble paper quality and a transparent water-soluble film sheet, and superimposing the sheets and processing the resulting product into a bag shape, as a waste collection bag.

JP 3142751 U discloses a waste collection bag including a water-soluble bag body made of a material obtained by foaming polyvinyl alcohol.

JP 2002-306522 A discloses a urine absorbing article for care in which a urine absorbing material in which a sheet having both water absorbency and water solubility is enclosed in a water-soluble bag is inserted into a pocket in a urine absorbing pad in which an inner fabric having water absorbency and an outer fabric having waterproofness are sewn with a dam interposed therebetween, another inner fabric having water absorbency is used at a central portion of the inner fabric, and a pocket is provided by sewing portions other than an opening portion.

JP 5841209 B2 discloses an excrement separating collector comprising a sheet-like water absorbent sheet portion attached to a crotch portion of a wearer and configured to absorb urine discharge of the wearer, a feces collection bag provided on a back surface side of the water absorbent sheet portion so as to be capable of collecting feces of the wearer and made of a material that can be dumped in a state where the feces is stored, and a feces collection bag accommodating portion provided on a back surface side of the water absorbent sheet portion and accommodating the feces collection bag, in which the feces collection bag includes a bag main body, a flange provided along a neck portion of the bag main body, and a check valve for preventing leakage of a collected matter, and a feces collection bag attachment hole communicating with a neck portion of the feces collection bag is formed on a back side of the water absorbent sheet portion positioned on a back side of the wearer during wearing, and, a groove is formed from a back side end of the water absorbent sheet portion to the feces collection bag attachment hole.

BRIEF SUMMARY

Technical Problem

Since the waste treatment bag described in JP 2000-34001 A, the disposable waste treatment article described in JP 3051660 U, and the waste collection bag described in JP 3142751 U are made of a water-soluble or water decomposable material, dissolution or decomposition proceeds even by moisture contained in the contents. Therefore, the contents may leak when unable to dump immediately after use. In addition, since the urine absorbing article for care described in JP 2002-306522 A can only collect urine, it is difficult to collect urine at the same time as defecation. In the excrement separating collector described in JP 5841209 B2, the water absorbent sheet and the feces collection bag are separated, and a caregiver or the like may touch the water absorbent sheet that has absorbed urine during treatment after use.

The present invention has been made in view of such problems, and an object of the present invention is to provide a moisture-retaining body that quickly dissolves or decomposes by coming into contact with a large amount of moisture when dumped in a flush toilet or the like while preventing dissolution or decomposition by retained moisture.

Solution to Problem

The present invention according to the above problems solves the above problems by providing a moisture-retaining body including: a water-absorbing surface; and a structure in which, in order from a side of the water-absorbing surface, a water-permeable layer formed of a papermaking body with a density of 40 to 60 $g/m^2$ and having water disintegrability and water permeability; a moisture-retaining layer having water disintegrability, water absorbability, and water retainability; a water-repellent layer including a water-soluble film and dots of a water-repellent resin with a diameter of 5 μm to 150 μm dispersed on a surface side of the water-soluble film facing the moisture-retaining layer; and a support layer formed of a papermaking body with a density of 40 to 60 $g/m^2$ and having water disintegrability are sequentially laminated, in which water disintegration rate of the support layer is higher than water disintegration rate of the water-permeable layer.

In the moisture-retaining body according to the present invention, the papermaking body forming the support layer and the water-permeable layer may be a papermaking body containing natural or regenerated cellulose fibers.

In the moisture-retaining body according to the present invention, the moisture-retaining layer preferably includes a porous water-absorbent material as the water-absorbent material.

In the moisture-retaining body according to the present invention, the moisture-retaining layer preferably further contains one or both of a dry hydrogel and a gelling agent.

In the moisture-retaining body according to the present invention, the moisture-retaining layer may further contain water-absorbing pulp, papermaking body, or cotton-like material.

Alternatively, the moisture-retaining body according to the present invention may further include a preliminarily water-absorbing layer containing water-absorbing pulp, a papermaking body, or a cotton-like material between the moisture-retaining layer and the water-repellent layer.

In the moisture-retaining body according to the present invention, the moisture-retaining layer preferably contains a biodegradable material.

Advantageous Effects of Invention

In the moisture-retaining body of the present invention, since moisture absorbed through the water-permeable layer provided on the water-absorbing surface is retained in the moisture-retaining layer, backflow of absorbed moisture from the water-absorbing surface can be suppressed. In addition, since the water-repellent layer is provided between the moisture-retaining layer and the support layer, leakage of absorbed moisture from the moisture-retaining layer to the support layer is suppressed. Moreover, since the water-permeable layer, the moisture-retaining layer, and the support layer all have water disintegrability, and the water-repellent layer includes a fine dot-like thin film of a water-soluble polymer and a water-repellent resin, the moisture-retaining body can be quickly dissolved or decomposed by being dumped in a flush toilet or the like after use, brought into contact with a large amount of moisture, or tossed by water flow. Therefore, the moisture-retaining body according to the present invention can be hygienically treated by being dumped in a flush toilet or the like after use while being prevented from being dissolved or decomposed by retained moisture during use.

Since the moisture-retaining body according to the present invention has the characteristics as described above, for example, it is possible to reduce risk of infection and the like at the time of collecting urine, feces, vomit and the like of humans and animals and labor of wiping and cleaning a private part, and it is possible to immediately dispose the moisture-retaining body to a toilet or the like after collection. In addition, the present invention is also applicable to ostomates and the like, and there is no need to worry about a cleaning place or a disposal place of a pouch contaminated after use even when going out, so that it is possible to reduce difficulty of the ostomate user due to going out or working.

DETAILED DESCRIPTION

Figure 1:
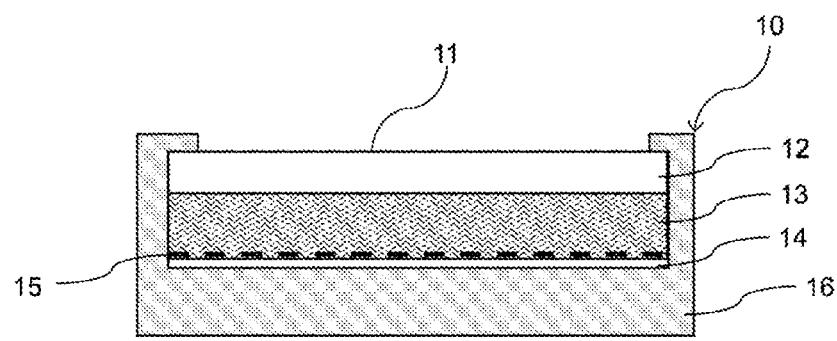
FIG. 1 is a schematic diagram showing a cross-sectional structure of a moisture-retaining body according to an embodiment of the present invention.

Hereinafter, embodiments of the present invention will be described with reference to the drawings. Note that. In the drawings, the same or equivalent portions are denoted by the same reference numerals.

As shown in FIG. 1, a moisture-retaining body (hereinafter, it may be abbreviated as a "moisture-retaining body".) 10 according to a first embodiment of the present invention is a member having a water-absorbing surface 11, and has a structure in which, from the water-absorbing surface 11 side, a water-permeable layer 12 having water disintegrability and water permeability, a moisture-retaining layer 13 having water disintegrability, water absorbability, and water retainability, a water-soluble film (hereinafter, it may be abbreviated as a "thin film".) 14, a water-repellent layer including dots 15 of a water-repellent resin with a diameter of 5 μm to 150 μm dispersed on a surface side of the thin film 14 facing the moisture-retaining layer 13, and a support layer 16 having water disintegrability are sequentially laminated. Each layer may have a sheet-like shape and have substantially the same shape. However, in order to prevent leakage of moisture from the side surfaces of the water-permeable layer 12 and the moisture-retaining layer 13, the side surfaces of both layers may be covered with the water-soluble film 14 on which the dots 15 of the water-repellent resin and the support layer 16 are formed, or the side surface of the moisture-retaining body 10 may be covered with another layer having no water permeability.

In the present invention, the term "water disintegrability" means that the sheet-like structure is disintegrated by coming into contact with a large amount of water (water with a volume several times (several tens of times) the volume of the moisture-retaining body 10) or being tossed by water flow. When the moisture-retaining body has water disintegrability, the moisture-retaining body can be dumped in a flush toilet after use, and can be treated hygienically. Therefore, it is preferable that the moisture-retaining body can be dumped in a flush toilet, and for example, it is preferable that the moisture-retaining body conforms to standards such as JIS P4501 ("toilet paper"), Guidelines for Assessing the Flushability of Disposable Nonwoven Products by the European Disposables And Nonwovens Association (EDANA) and the Association of the Nonwoven Fabrics Industry (INDA), and the IWSFG Flushability Specifications. In light of the nature of the moisture-retaining body 10 that is used in the fields of care, nursing, childcare, pet supplies, and the like, the moisture-retaining body 10 is preferably soluble in cold water of about 0° C. in order to enable use in cold areas. In addition, it is preferable that the moisture-retaining body 10 is quickly disintegrated by water flow at the time of flashing after immersion in sealed water of the flush toilet for about 30 seconds. Moreover, it is preferred that the fine residue remaining after flashing is also completely dissolved or disintegrated with water within 3 minutes.

Water-Permeable Layer

The water-permeable layer 12 is a sheet-like layer in which one surface side is exposed to the outermost layer and acts as the water-absorbing surface 11, and the opposite surface side is in contact with the moisture-retaining layer 13 described later. The water-permeable layer 12 has water disintegrability and water permeability. The term "water permeability" refers to a property of allowing water absorbed from the water-absorbing surface to permeate the surface opposite to the water-absorbing surface and guiding the absorbed moisture to the moisture-retaining layer 13, and as a result, moisture absorbed by the water-permeable layer 12 is retained, thereby making it possible to prevent discomfort from being given to a user and prevent moisture from seeping from the water-permeable layer 12 when receiving pressure.

The water-permeable layer 12 is preferably formed of, for example, a papermaking body having water permeability and water disintegrability from the viewpoint of water disintegrability. In addition, in consideration of environmental load and applicability to flush toilets, it is preferable that the material forming the papermaking body does not contain a synthetic resin, is a material derived from a natural product, and/or has biodegradability. Specific examples of preferable materials forming the papermaking body include natural cellulose derived from wood, cotton, herbs, bamboo, and the like, pulp derived from the above-mentioned natural resources or waste paper, and regenerated cellulose such as copper ammonia rayon (cupra), viscose rayon, polynosic, and lyocell. The fiber diameter is, for example, 5 to 200 μm, and the fiber length is 0.1 to 7 mm. These materials can be used alone, but from the viewpoint of improving water disintegrability, it is preferable to use a hybrid material of a plurality of materials having different fiber diameters, fiber lengths, and expansion rates when coming into contact with moisture, a hybrid material of different materials, or the like.

Specific examples of the papermaking body include nonwoven fabric or paper (water-disintegrated paper), and the like. The fiber diameter and the fiber length of the fiber material used for papermaking are not particularly limited as long as the fiber material has desired water permeability and water disintegrability. The thickness of the water-permeable layer 12 and the density of the papermaking body are appropriately determined in consideration of desired mechanical strength and a constituent material of a water-absorbing surface that is in direct contact with the body of the user during use. However, in consideration of mechanical strength, comfort of the user, and the like, a water-disintegrable nonwoven fabric with a density of about 40 to 60 g/m² is preferable.

Moisture-Retaining Layer

The moisture-retaining layer 13 is a sheet-like layer that is in contact with a first water-permeable layer 12 on one side and the water-repellent layer 15 on the opposite side, and includes a water-absorbent material having water disintegrability, water absorbability, and water retainability. The moisture-retaining layer is configured to retain absorbed moisture for a desired time, more specifically, at least for a time until the moisture-retaining body 10 is dumped, and be quickly disintegrated when the moisture-retaining body 10 is dumped in a flush toilet or the like after use and comes into contact with a large amount of water or is tossed by water flow. For example, the moisture-retaining layer includes a porous water-absorbent material and a dry hydrogel. Examples of the porous water-absorbent material include fine particulate porous materials made of natural or synthetic materials such as sponge, superabsorbent polymer (sodium polyacrylate, and the like), sea sponge, and food residue, but considering dumping in a flush toilet or the like, porous materials made of materials derived from natural products are preferable, and porous materials having biodegradability are more preferable.

Specific examples of preferred porous water-absorbent material include soybean skin dried after milking, dried potato, and the like. The porous material forming the moisture-retaining layer has, for example, a particle diameter of 30 μm and a density of about 0.4.

The dry hydrogel includes a matrix mainly composed of a polymer or low-molecular assembly having a crosslinked structure, and has an action of absorbing moisture absorbed from an absorption surface together with a porous water-absorbent material, absorbing a large amount of water to swell when coming into contact with a large amount of water or being tossed by water flow, and assisting disintegration of the moisture-retaining layer due to a difference in swelling rate from the porous water-absorbent material. Examples of the material of the dry hydrogel include crosslinked acrylamide, alga-derived polysaccharides (agar), and the like.

The smaller the particle size of the fine particulate porous material, the larger the surface area and the larger the water absorption amount per unit volume can be, but the surface energy may increase, and problems such as secondary aggregation and poor handling may occur, so that the particle size is appropriately adjusted. A preferred particle size of the porous material is, for example, 30 μm to 200 μm. The mixing ratio of the porous material and the dry hydrogel is, for example, porous material:dry hydrogel=3:2.

When a natural material is used as the porous water-absorbent material and the material of the dry hydrogel material, it is preferable to blend an antiseptic agent, an antibacterial agent, or the like for improving storage stability and preventing decay. Specific examples of the antiseptic agent and the antibacterial agent include benzoate, sodium percarbonate, benzalkonium chloride, and the like.

The moisture-retaining layer 13 may contain fluff pulp. In either of the case where the moisture-retaining layer contains or does not contain fluff pulp, a preliminarily water-absorbing layer (not shown) containing fluff pulp may be provided between the moisture-retaining layer and the water-repellent layer. The material and fiber diameter of the fluff pulp are basically the same as those of the pulp used as the material of the papermaking body forming the water-permeable layer 12 described above. Regarding the fiber length, it is preferable that the fiber length is larger than that of the material used as the material of the papermaking body in view of the need to exhibit fluffy properties, and it is preferable that the fiber length is, for example, 10 mm or more and 30 mm or less in consideration of balance with water disintegrability.

Water-Soluble Film and Water-Repellent Layer

A water-soluble film 14 is provided between the moisture-retaining layer 13 or the preliminarily water-absorbing layer and a support layer 16 to be described later, and on a surface of the water-soluble film 14 on the moisture-retaining layer 13 side, a water-repellent layer including the dots 15 of the water-repellent resin with a diameter of 5 μm to 150 μm is formed so as to be distributed substantially uniformly or in a predetermined pattern on the surface. When the moisture-retaining body 10 is used, the water-repellent layer prevents moisture retained in the moisture-retaining layer 13 from seeping into the support layer 16 and prevents leakage of moisture and disintegration of the support layer 16, and when the water-repellent layer is dumped after use of the moisture-retaining body 10, and comes into contact with a large amount of moisture that has been permeated from the support layer 16 side, the water-soluble film 14 is dissolved, and flow out of the dots 15 of the water-repellent resin allows the moisture-retaining body 10 to quickly disintegrate with water. In other words, forming the water-repellent layer including the water-soluble film 14 and the dots 15 of the water-repellent resin as described above allows the moisture-retaining body 10 to achieve both a high moisture-retaining function and ease of treatment after use.

Examples of the material of the water-soluble film 14 include starch, gelatin, carrageenan, guar gum, carboxymethyl cellulose, polyacrylic acid, polyvinyl pyrrolidone, polyvinyl alcohol (PVA), and the like. The type of material, molecular weight, thickness of the water-soluble film, and the like are appropriately selected according to the water solubility required for the water-soluble film 14 (dissolution also in cold water around 0° ° C. considering desired dissolution rate and use in cold areas, and the like).

The water-repellent layer 15 is formed on one side of the water-soluble film 14 by forming dots (diameter: 5 μm to 150 μm) of the water-repellent resin on the surface of the water-soluble film 14 by a method such as an inkjet printing method or an intaglio printing such as a gravure printing method. With such a configuration, a fractal structure can be imparted to the water-repellent surface, a contact angle with a water droplet can be increased, and high water repellency can be exhibited, and when the water-soluble film 14 is dissolved by being brought into contact with a large amount of water after using the moisture-retaining body 10, fine dots of the water-repellent resin are formed, and an insoluble residue is not left, so that the water-repellent resin can be dumped in a flush toilet or the like without any problem. The water-repellent layer 15 is not necessarily required to cover the entire surface of the water-soluble film 14, and may cover at least a part thereof. As the material of the water-repellent resin, any material that can be printed on the surface of the water-soluble film 14 and has hydrophobicity can be used without particular limitation, but a biodegradable resin such as polylactic acid or bio-polyurethane is preferable.

Support Layer

The support layer 16 is a sheet-like layer that is located on the opposite side of the water-absorbing surface, serves a function of the moisture-retaining body 10 as a base material, and has water disintegrability. The material forming the support layer 16 is equivalent to the papermaking body forming the water-permeable layer 12, but in view of the function of the moisture-retaining body 10 as the base material, the fiber length of the water-disintegrable fiber is preferably shorter than that of the water-permeable layer 12, and it is preferable that the water-disintegrable fiber is not in contact with water during use of the moisture-retaining body 10, but comes into contact with a large amount of water during disposal after use, or is quickly disintegrated with water when tossed by water flow. Therefore, the water disintegration rate is further preferably higher than that of the papermaking body forming the water-permeable layer 12, and when it is necessary to minimize the residue discharged from the toilet, a papermaking body of natural fiber and carboxymethyl cellulose can also be selected.

Production Method

Figure 2:
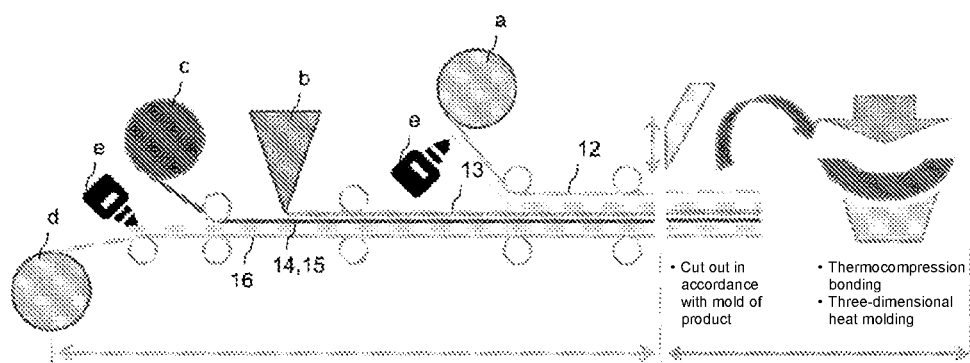
FIG. 2 is a schematic diagram showing an example of a method for producing a moisture-retaining body.

For example, as shown in FIG. 2, a first papermaking body (a) forming the water-permeable layer 12, a second papermaking body (d) forming the support layer 16, and a water-soluble film 14 (c) having the water-repellent layer 15 formed on one side thereof by an inkjet printing method or the like are continuously supplied from a roll, and between the first papermaking body (a) forming the water-permeable layer 12 and the water-soluble film 14 (c) having dots 15 of the water-repellent resin formed on one side thereof, a dry hydrogel, a porous material, and fluff pulp (b), which are constituent materials of the moisture-retaining layer 13 (preliminarily water-absorbing layer as necessary), are rolled while being supplied, whereby a sheet-like laminate is continuously produced, cut out in accordance with the size and shape of a product, thermocompression bonding, and three-dimensional heat molding are performed as necessary to obtain a moisture-retaining body 10 having a desired size and three-dimensional shape. The sheet-like material forming each layer is bonded via adhesive layers provided at both ends along the longitudinal direction or by applying an adhesive (e) as shown in FIG. 2. The base, pressure sensitive adhesive, and adhesive of the adhesive layer need to have water solubility, and preferably have biodegradability.

Application

The moisture-retaining body 10 produced as described above can be used in the fields of care, nursing care, childcare, pet supplies, and the like.

EXAMPLES

Example 1: Production of Moisture-Retaining Body

A sheet-like (19×8×0.489 cm) moisture-retaining body including the following materials was produced by the method shown in FIG. 2.

Water-permeable layer: Water-disintegrable nonwoven fabric (manufactured by Oji F-Tex Co., Ltd.: 46 g/m$^2$)
Moisture-retaining layer: Mixture of following things
Dry hydrogel (dry agar) 20.2 wt %
Porous water-absorbent material: Soybean skin dried after milking 30.3 wt %
Antiseptic/fungicide: Sodium percarbonate 5.1 wt %
Fluff pulp 44.4 wt %
Water-soluble film: Cold water soluble polyvinyl alcohol (manufactured by AICELLO CORPORATION)
Water repellent: Bio-polyurethane (diameter 50 to 130 μm, thickness 1 μm) with gravure coating on the surface of water-soluble film
Support layer: Water-soluble paper (manufactured by ONAO CO., LTD: 50 g/m$^2$)
Adhesive: Casein Examples 2: Performance Evaluation of Moisture-Retaining Body (1) Water Absorbency and Water Leakage Test 50 mL of tap water was gently poured onto the water-absorbing surface of the moisture-retaining body, and after leaving for 30 seconds, it was visually confirmed, and as a result, peeling of each layer and water leakage from the surface opposite to the water-absorbing surface and the side surface were not observed.

(2) Water Disintegrability Test

The moisture-retaining body after the water absorbency and water leakage test was put into 1000 mL of tap water at 11° C., left for 15 seconds, and then stirred for 15 seconds. As a result of visually observing properties of the aqueous solution, no lump residue was observed, and it was observed that the constituent material of the moisture-retaining body was uniformly dispersed in water. As a result of filtering the aqueous solution and observing properties of the solid content, no lump residue was observed.

(3) Water Disintegrability Test Using Flowing Water

The water disintegrability of the moisture-retaining body produced in Example 1 was evaluated using a water disintegrability test evaluation apparatus manufactured by NISSIN KIKAI Co., Ltd. 2 L of water (15±1° C.) was put in a cell of the water disintegrability test evaluation apparatus, the moisture-retaining body was put therein, and then the apparatus was started and shaken at 18 rpm for 30 minutes.

The moisture-retaining body after shaking was received on a φ 12.5 mm perforated plate sieve, and 4 L/min of water was sprayed from a height of 10 cm using a shower head for 90 seconds. The dry weight of the residue on the perforated plate sieve was measured. As a result, the dry weight of the residue remaining on the perforated plate sieve was 1% or less (among the six samples tested, no residue was observed for four.) of the dry weight of the moisture-retaining body. These results cleared the criteria of EDAMA/INDA and the evaluation criteria of IWSFG adopted by Japan Sewage Works Association, and it was confirmed that there was no problem with dumping in flush toilets and sewers.

REFERENCE SIGNS LIST 10 moisture-retaining body
11 water-absorbing surface
12 water-permeable layer
13 moisture-retaining layer
14 water-soluble film
15 dot of water-repellent resin
16 support layer
a first papermaking body
b constituent material of moisture-retaining layer
c water-soluble film in which dots of water-repellent resin are formed on one side
d second papermaking body
e adhesive

The invention claimed is:

1. A moisture-retaining body comprising:
    a water-absorbing surface; and
    a structure in which, in order from a side of the water-absorbing surface,
        a water-permeable layer formed of a papermaking body with a density of 40 to 60 g/m$^2$ and having water disintegrability and water permeability;
        a moisture-retaining layer having water disintegrability, water absorbability, and water retainability;
        a water-repellent layer including a water-soluble film and dots of a water-repellent resin with a diameter of 5 μm to 150 μm dispersed on a surface side of the water-soluble film facing the moisture-retaining layer; and
        a support layer formed of a papermaking body with a density of 40 to 60 g/m$^2$ and having water disintegrability are sequentially laminated,
    wherein water disintegration rate of the support layer is higher than water disintegration rate of the water-permeable layer.

2. The moisture-retaining body according to claim 1, wherein the papermaking body forming the support layer and the water-permeable layer is a papermaking body containing natural or regenerated cellulose fibers.

3. The moisture-retaining body according to claim 1, wherein the moisture-retaining layer includes a porous water-absorbent material as a water-absorbent material having the water absorbability.

4. The moisture-retaining body according to claim 3, wherein the moisture-retaining layer further contains one or both of a dry hydrogel and a gelling agent.

5. The moisture-retaining body according to claim 1, wherein the moisture-retaining layer contains water-absorbing pulp, papermaking body, or cotton-like material.

6. The moisture-retaining body according to claim 1, further comprising a preliminarily water-absorbing layer containing water-absorbing pulp, a papermaking body, or a cotton-like material between the moisture-retaining layer and the water-repellent layer.

7. The moisture-retaining body according to claim 1, wherein the moisture-retaining layer contains a biodegradable material.

8. The moisture-retaining body according to claim 1, wherein the moisture-retaining layer includes:
    a porous water-absorbent material,
    one or both of a dry hydrogel and a gelling agent, and
    a water-absorbing pulp, papermaking body, or cotton-like material.

* * * * *